United States Patent

Roe et al.

[11] Patent Number: 5,966,217
[45] Date of Patent: Oct. 12, 1999

[54] SYSTEM AND METHOD FOR DISTINGUISHING AN ITEM FROM A GROUP OF ITEMS

[75] Inventors: Mitchell Gregg Roe, Franklin; Garry R. Kenny, College Grove, both of Tenn.

[73] Assignee: Magnetic Separation Systems, Inc., Nashville, Tenn.

[21] Appl. No.: 08/934,828

[22] Filed: Sep. 22, 1997

[51] Int. Cl.$^6$ .............................. G01J 3/46; G01J 21/25; G01N 21/25; B07C 5/00; B07C 5/342

[52] U.S. Cl. ................ 356/402; 356/407; 356/239.4; 356/239.1; 209/524; 209/576; 209/580

[58] Field of Search ........................... 209/44.1; 356/240, 356/407

[56] References Cited

U.S. PATENT DOCUMENTS

| | | | |
|---|---|---|---|
| 5,141,110 | 8/1992 | Trischan et al. | 356/240 |
| 5,150,307 | 9/1992 | McCourt et al. | 356/240 |
| 5,223,917 | 6/1993 | Richert | 356/407 |
| 5,314,072 | 5/1994 | Frankel et al. | 209/44.1 |
| 5,318,172 | 6/1994 | Kenny et al. | 356/240 |
| 5,443,164 | 8/1995 | Walsh et al. | 356/240 |
| 5,502,559 | 3/1996 | Powell et al. | 356/73 |
| 5,536,935 | 7/1996 | Klotzsch et al. | 356/240 |

OTHER PUBLICATIONS

"A Two–Colour Near–infrared Sensor for Sorting Recycled Plastic Waste".

Primary Examiner—Frank G. Font
Assistant Examiner—Roy M. Punnoose
Attorney, Agent, or Firm—Waddey & Patterson; Edward D. Lanquist, Jr.

[57] ABSTRACT

The present invention discloses an electromagnetic source which transmits electromagnetic radiation to an object. The electromagnetic radiation then either passes through the object or is reflected by the object depending upon the electromagnetic source and the type of the object. The reflected or penetrating radiation, depending upon the type of application, is picked up by a receiver. The receiver then sends the penetrating or reflected signal into a splitter which divides it into a first and second stream or a third and fourth stream, if necessary. After each of these streams, the split signal can then be run through a filter before it is analyzed by a sensor. The sensor reading is then fed into a microprocessor which compares, combines, and evaluates the various readings.

13 Claims, 6 Drawing Sheets

SYSTEM AND METHOD FOR DISTINGUISHING AN ITEM FROM A GROUP OF ITEMS

BACKGROUND OF THE INVENTION

The present invention relates generally to a sorting system and more particularly to a system using an electromagnetic radiation source to separate one item from a plurality of items.

It will be appreciate by those skilled in the art that items such as plastic and paper need to be recycled. Unfortunately, when it is received at a recycling station, this material is often commingled so that plastic and paper are commingled as well. Additionally, plastics of various types are also commingled. To this end, there have been several attempts to sort these materials. One such attempt is described in the Meas. Sci. Technology in 1995 which discloses a 2-color near-infrared sensor for sorting recycled plastic waste. This particular descriptions uses a split near infrared region of the electromagnetic spectrum to sort different types of polymers. This particular item explains how PET and PVC can be distinguished. Unfortunately, this disclosure uses a beam splitter which is very ineffective and can be difficult to use in the field because it must be fabricated to a suitable tolerance. Also, the angle must be maintained carefully to assure a good split. Additionally, the splitter required in the disclosure must be electroplated with gold. As a result, it can be very expensive. The hardware implementation specified in this paper uses a logarithmic amplifier in an attempt to measure the actual absorbence of a material. In reality, this technique is not practical because it assumes that the material being measured is perfectly clean and has a negligible reflectance. This is clearly not the case for a post-consumer recycling application.

What is needed, then, is a system and method for distinguishing items from a plurality of items. This needed system must be easy to use in the field and efficient to manufacture. This needed system must be capable of reading multiple wavelengths. This system is presently lacking in the prior art.

SUMMARY OF THE INVENTION

The present invention discloses an electromagnetic source which transmits electromagnetic radiation to an object. The electromagnetic radiation then either passes through the object or is reflected by the object depending upon the electromagnetic source and the type of the object. The reflected or penetrating radiation, depending upon the type of application, is picked up by a receiver. The receiver then sends the penetrating or reflected signal into a splitter which divides it into a first and second stream or a third and fourth stream, if necessary. After each of these streams, the split signal can then be run through a filter or series of filters before it is analyzed by a sensor. The sensor reading is then fed into a microprocessor which compares, combines, and evaluates the various readings.

Accordingly, one object of the present invention is to provide a system and method for distinguishing an item from a plurality of items.

Another object of the present invention is to provide a system which is easy to manufacture.

Still a further object of the present invention is to provide a system which is durable in the field.

Another object of the present invention is to provide a system for sorting polyethylene terephthalate (PEI) from polyethylene naphthalate (PEN).

Another object of the present invention is to provide a system for sorting PET from polyvinylchloride (PVC).

Another object of the present invention is to provide a system for sorting clear containers from light blue containers.

Another object of the present invention is to provide a system for sorting clear containers, light blue containers, light green containers, dark green containers, blue-green containers, and amber containers.

Another object of the present invention is to separate paper containers from plastic containers.

DESCRIPTION OF THE PREFERRED EMBODIMENTS

Figure 1:
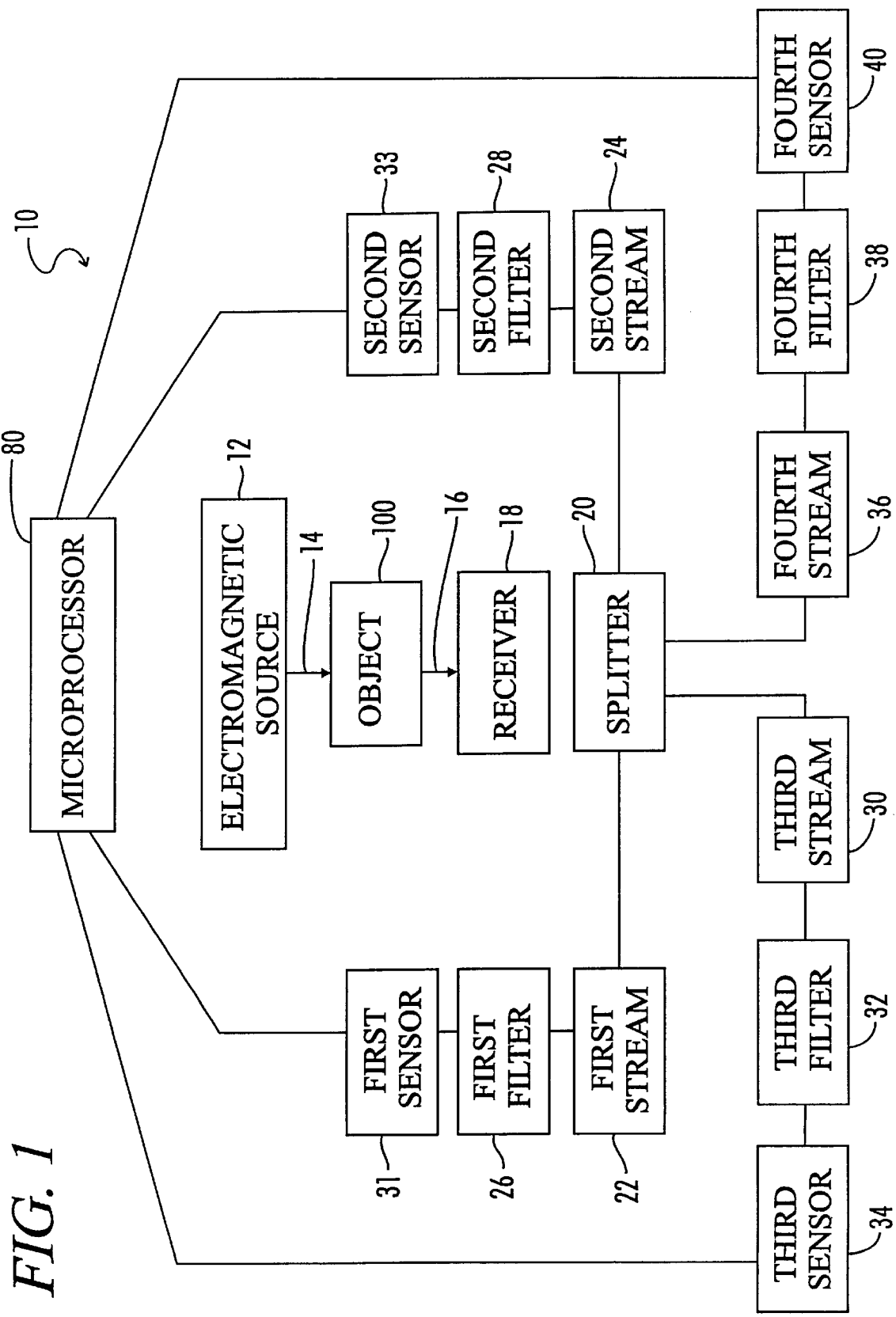
FIG. 1 is a block diagram of the transmission system and method of the present invention.

Referring now to FIG. 1, there is shown generally at 10 the system and method for distinguishing an item from a plurality of items. This particular block diagram shows the transmission system. As can be seen, electromagnetic source 12 creates and transmits the electromagnetic radiation 14 to an object 100. Penetrating electromagnetic radiation 16 is then received by receiver 18 which transmits the signal into splitter 20. Splitter 20 preferably, splits the stream into first stream 22 and second stream 24. Each stream contains the required band width of electromagnetic radiation. However, splitter 20 can also split into additional third stream 30 and fourth stream 36. After splitter 20 splits signal into first stream 22, signal is passed through first filter 26 into first sensor 31. First sensor 31 is then electronically connected to microprocessor 80. Similarly, second stream 24 is directed through second filter 28 into second sensor 33 which is electronically connected to microprocessor. Likewise, third stream 30 is directed through third filter 32 to third sensor 34 into microprocessor 80. Finally, fourth stream 36 is directed through fourth filter 38 into fourth sensor 40 which is electronically connected to microprocessor 80. likewise, there can be an nth stream.

Figure 2:
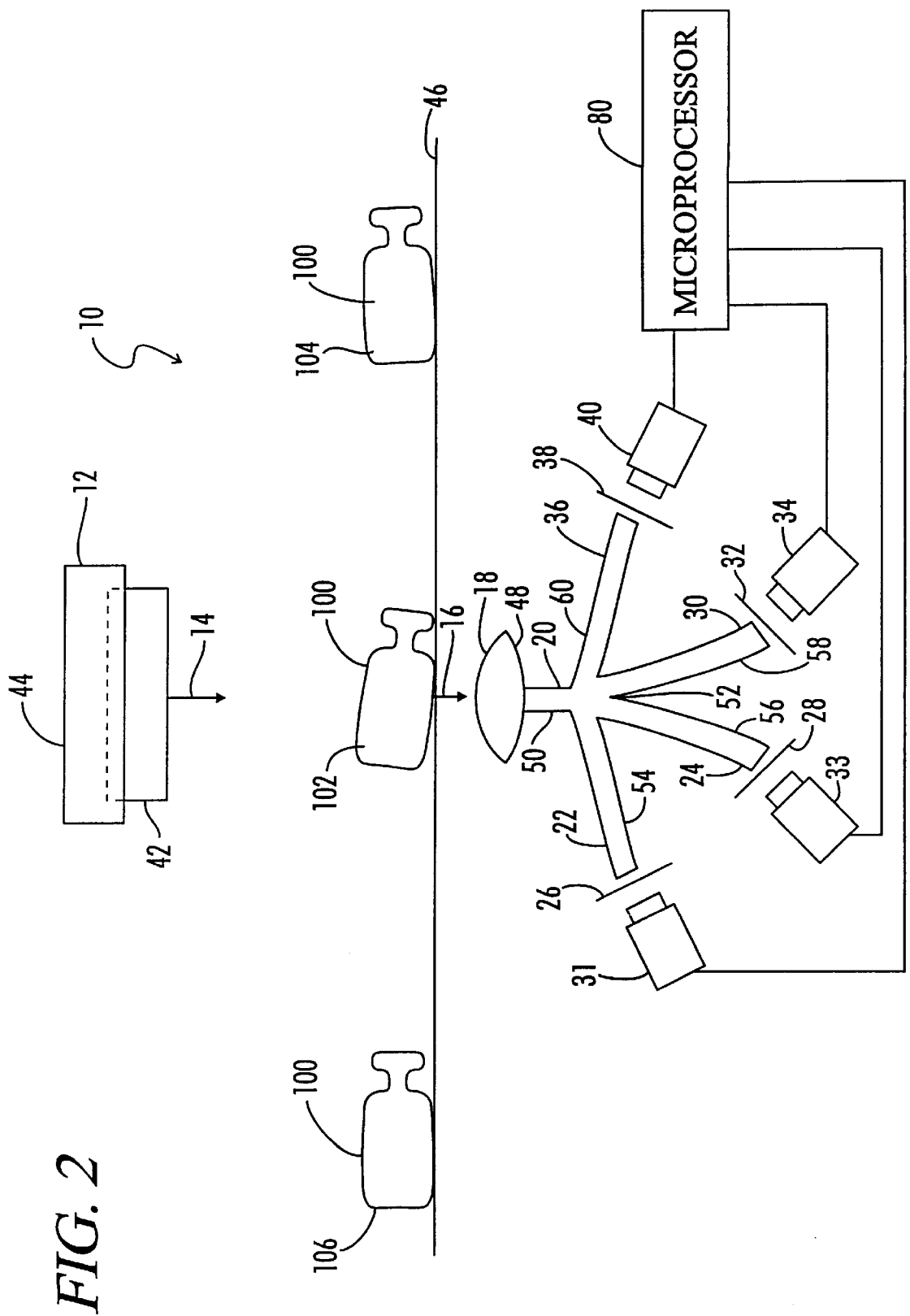
FIG. 2 is a side view of the system and method of the transmission system and method of the present invention.

FIG. 2 shows a diagram of the transmission system of the present invention 10. As can be seen, electromagnetic source 12 is, often times, lamp 42 having housing 44 which creates transmitted electromagnetic radiation 14 through object 100. Object 100 can be first item 102, second item 104, or $n^{th}$ item 106. Penetrating electromagnetic radiation 16 which is transmitted electromagnetic radiation 14 which passes through object 100 is received by receiver 18 which is preferably lens 48. Lens 48 is connected to splitter 20 which is, preferably, fiberoptic cable 50 such as that manufactured by Cuda Products Corp., having first leg 54, second leg 56, third leg 58, and fourth leg 60. First leg 54 transmits first stream 22 of electromagnetic radiation through first filter 26 onto first sensor 31 which is electronically connected to microprocessor 80. Likewise, respectively, second leg 56, third leg 58, and fourth leg 60 pass respective streams 24, 30, and 36 of electromagnetic radiation through respective filters 28, 32, and 38, into respective sensors 32, 34, and 40.

Figure 3:
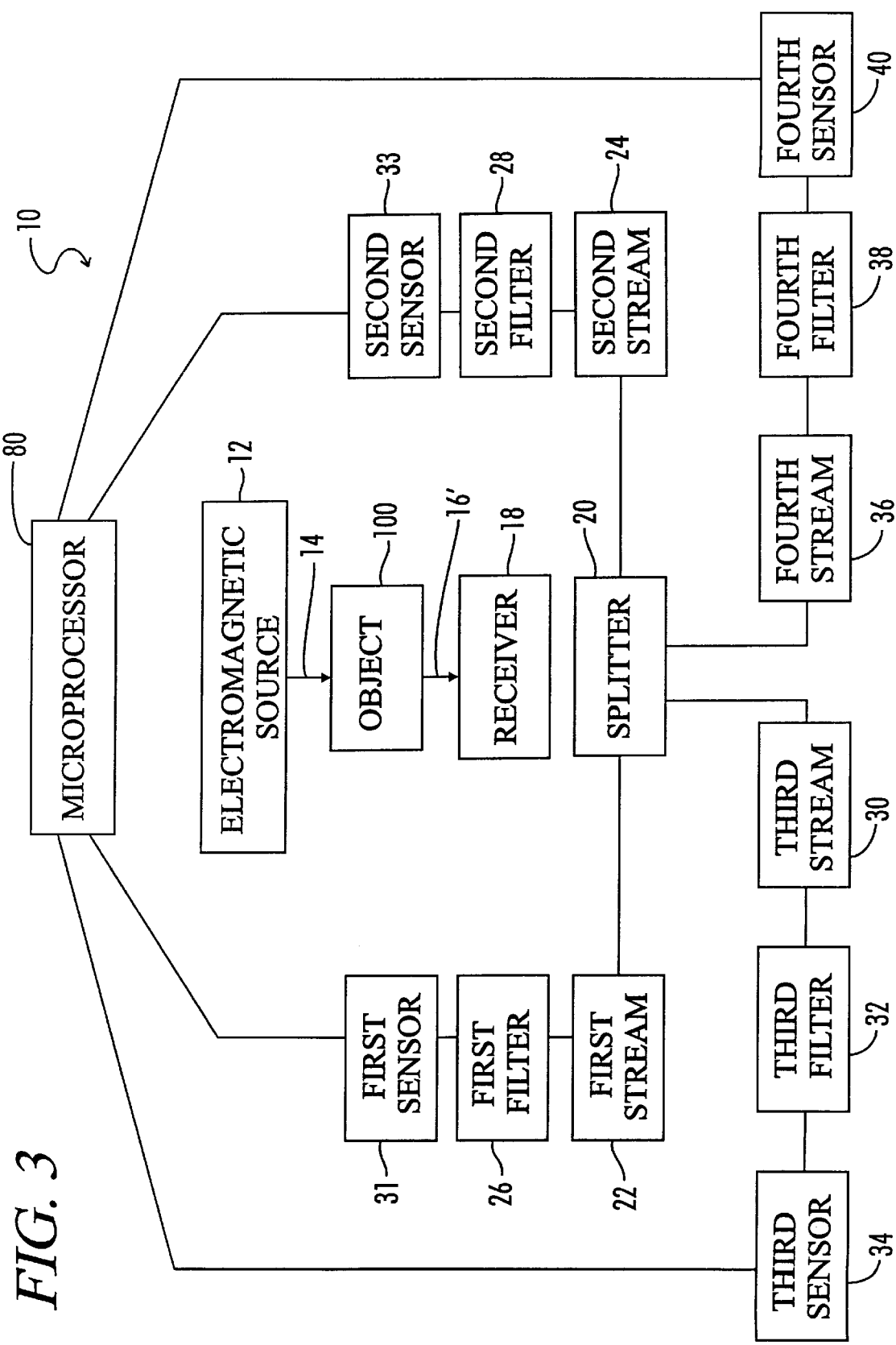
FIG. 3 is a block diagram of the reflective system of the present invention.
Figure 4:
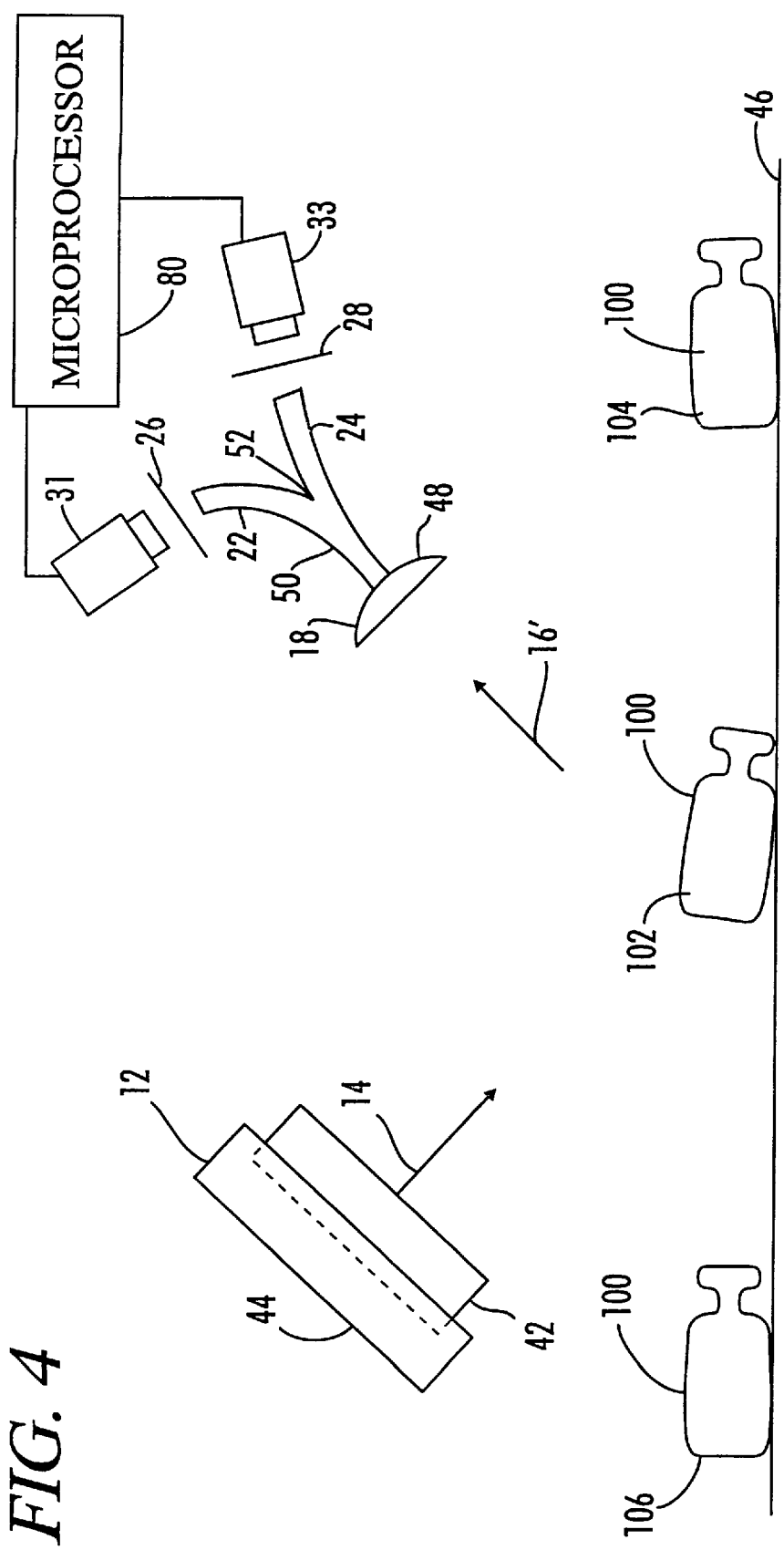
FIG. 4 is a side view of the reflective system and method of the present invention.

Referring now to FIG. 3, there is shown generally at 10 the block diagram of the reflective system and method of the present invention. As can be seen, FIG. 3 generally tracks FIG. 1 except transmitted electromagnetic radiation (16 in FIG. 1) is now reflected electromagnetic radiation 16'. Likewise, in FIG. 4, transmitted electromagnetic radiation (16 in FIG. 2) is now reflected electromagnetic radiation 16' in FIG. 4. FIG. 4 shows only first stream 22 and second stream 24. However, multiple streams can be provided.

The type of electromagnetic radiation and filter that are used will depend upon the type of material to be sorted. For example, when PET is sorted from PEN, differing types of electromagnetic radiation can be used. In a preferred embodiment, the electromagnetic source is ultra-violet light. The ultra-violet light, in the preferred embodiment, is created by a lamp such as that manufactured by Welch Allyn. The light is transmitted through the object and into the splitter. The first stream is run through a filter of substantially 380 nanometers while the second stream is fed through a filter of substantially 400 nanometers. The filters are preferably narrow band interference filters. The ratio of the amount of energy passing through the 380 nanometer filter is divided by the amount of energy passing through the 400 nanometer filter. If the ratio approaches "1", the item can be classified as a PET bottle. If the ratio approaches "0", the item can be classified as PEN.

Similarly, an infrared source can also be used to sort PEN from PET. The infrared source, in the preferred embodiment, is created by a lamp such as that manufactured by Sylvania. The penetrating infrared radiation is fed into a first stream or the second stream. The first stream is run through a filter of preferably 1660 nanometers whereas the second stream is fed through a filter of substantially 1670 nanometers. The ratio of the readings passing through the 1660 filter is divided by the readings passing through the 1670 filter. As this ratio approaches 0.8, the item is classified as PET. As the ratio approaches 1.1, the item is classified as PEN.

Still another method of distinguishing PET from PEN is to create electromagnetic radiation in a broader band such as that created by the lamp manufactured by Welch Allyn. The penetrating broad band electromagnetic radiation is then split into a first stream, a second stream, a third stream, and a fourth stream. The first stream is preferably a 380 nanometer filter. The second stream is fed through a 390 nanometer filter. The third stream is fed through a 430 nanometer filter. The fourth stream is fed through a 900 nanometer filter. The algorithm to compare these is as follows. If all four signals are substantially the same, then it is PET. If 380 and 390 are low compared to 430 and 900, then it is PEN. Ratios of 380/390 and 390/430 can be used to identify the ratio of PEN/PET in a container.

A still further method of sorting PET and PEN is to create fluorescence electromagnetic radiation using an ultra-violet lamp such as that manufactured by Raytech. The fluorescent light is then collected off of the object and sent into a splitter. The first stream of the filter is fed through a filter of substantially 390 nanometers. The second stream is fed through a filter of substantially 425 nanometers. The amount of energy through the first stream is divided by the amount of energy passed through the second stream. If this ratio approaches 0.2, the item is classified as PET. If this ratio approaches 0.4 or higher, it is classified as PVC.

Likewise, this system can be used to sort PET from PVC. This is especially a good sort when PET needs to be removed from a PVC stream. An infrared source is created by a lamp such as that manufactured by Sylvania. The amount of electromagnetic radiation penetrated through the object is split into a first stream and a second stream. The first stream is run through a filter of substantially 1670 nanometers. The second stream is fed through a filter of substantially 1720 nanometers. If the amount of electromagnetic radiation passing through the 1670 nanometer filter is low, then the object is classified as PET. If the amount of energy passing through the 1720 filter is low, then the object is classified as PVC. If there is an anonymous reading, then the object is treated as PVC and will flow through the path without being ejected.

Likewise, clear PET can be distinguished from light blue PET using an electromagnetic radiation source of visible light such as that created by the lamp manufactured by Sylvania. The electromagnetic radiation penetrating through the object is fed into a first stream and a second stream. The first stream is fed through a green filter of substantially 510 nanometers. The second stream is fed through a red filter of substantially 633 nanometers. If the amount of electromagnetic radiation passing through the red filter is low, the item is classified as light blue. If the amount of energy passing through the green filter is the same or low, the object is classified as clear.

Paper containers such as milk cartons can be distinguished from plastic containers such as bottles by using an infrared reflective system. In the preferred embodiment, infrared radiation is created by a lamp such as that manufactured by Welch Allyn. The infrared radiation is reflected from the object and directed into the splitter using the lamp. The first stream is passed through a filter of substantially 1470 nanometers. The second stream is passed through a filter of substantially 1730 nanometers. If the 1470 nanometer filter is low, the item is considered a milk carton. If the 1750 nanometer filter is low, the item is considered a plastic bottle.

The present system also allows for multiple classification. For example, if one wishes to perform a sort of clear, light blue, light green, dark green, blue-green, and amber containers, a visible light source created by a lamp such as that manufactured by Sylvania is used. The amount of penetrating electromagnetic radiation is split into four streams. The first stream is directed through a blue-violet 450 nanometer filter. The second stream is passed through a green 500 nanometer filter. The third stream is passed through a red filter of substantially 630 nanometers. The fourth stream is passed through a second red filter of substantially 680 nanometers. The readings for these various readings are as follows:

All four substantially the same → Clear
680 near zero and 450 low → Green or Blue-Green
680 and 450 near zero → Amber
450, 630, and 680 low → Green (European)
680 and 450 low → Light-Green
630 or 680 low → Light-Blue
450 and 500 low → Amber (European)

Figure 5A:
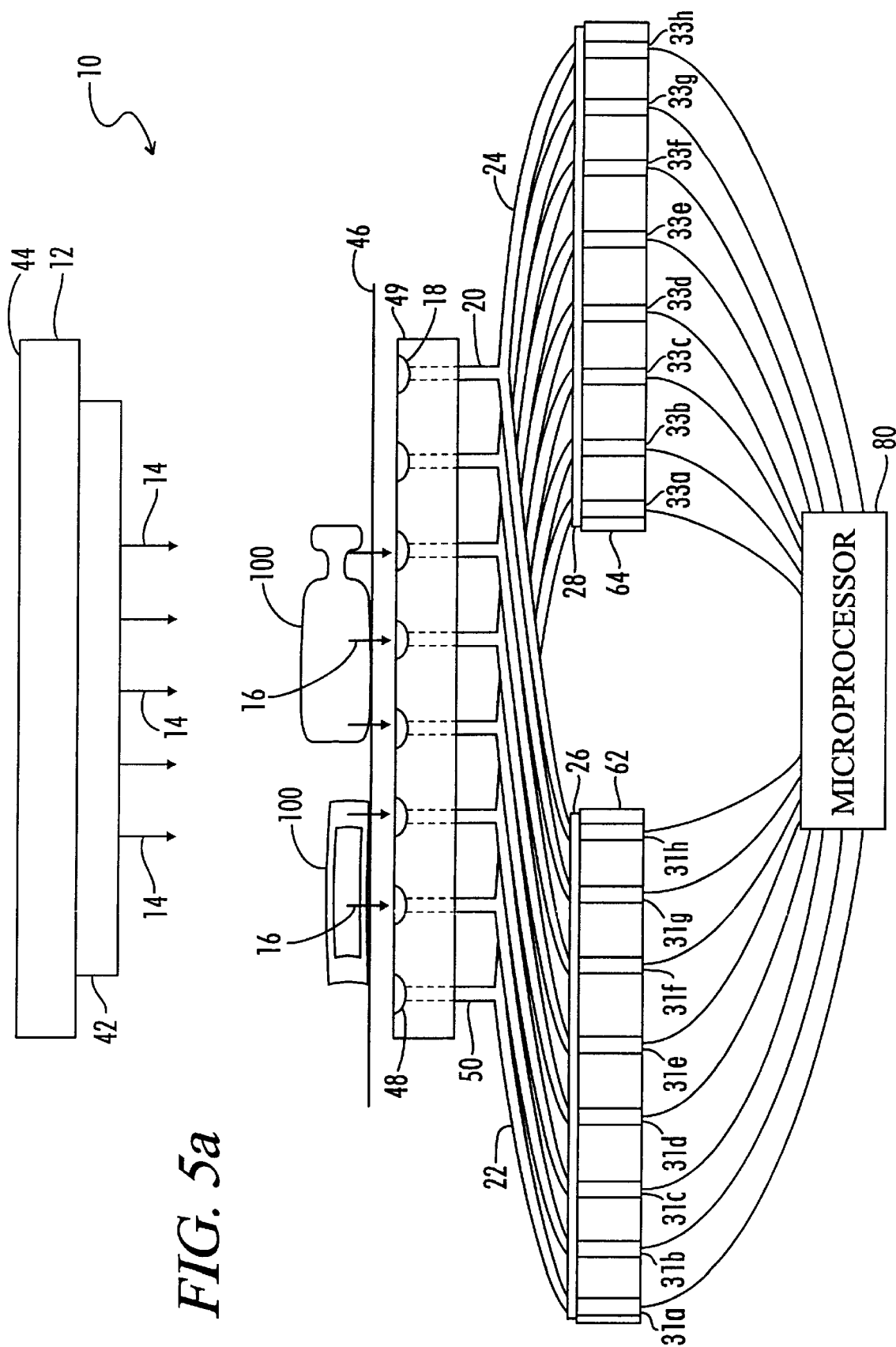
FIGS. 5a-5c are views of a system for sorting many items at once.
Figure 5B:
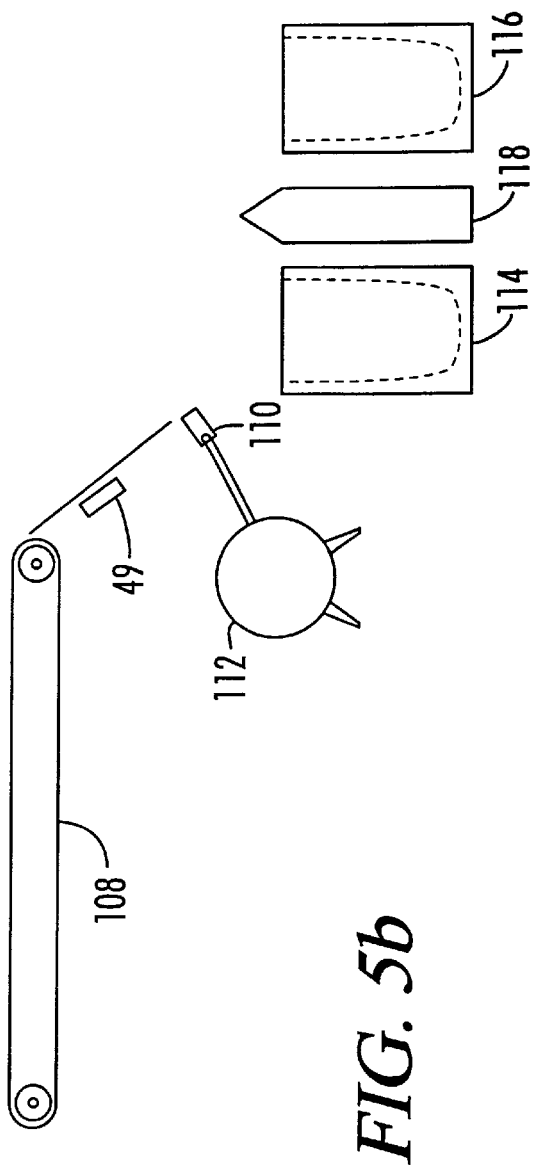
Figure 5C:
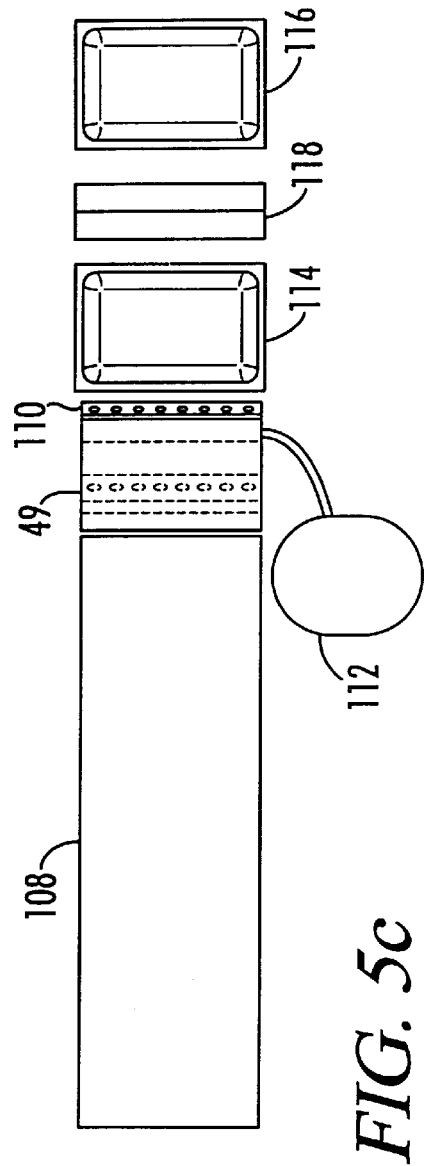

Referring now to FIG. 5a–c, there is shown generally at 10, a multiple sensor embodiment of the present invention. Electromagnetic radiation 14 is created as described above using electromagnetic source 12 which is preferably lamp 42 in housing 44. Some of the differing types of electromagnetic radiation are discussed above. Objects 100 travel across wear cover 46 and receive electromagnetic radiation 14 which is, in this embodiment, transmitted firough object 100 so that penetrating electromagnetic radiation 16 is received by receiver 18 which is in this embodiment lens 48 housed in lens board 49. Splitter 20 which is preferably fiberoptic cable 50 splits each received amount of penetrating electromagnetic radiation 16 into first stream 22 and second stream 24. However, additional streams (30, 36 in other Figures) can also be created. First stream 22 from each splitter 20 is directed through first filter 26 into a corresponding first sensor 31 *a–h* in first sensor array 62 which in turn are electronically connected to microprocessor 80. Second stream 24 from each splitter 20 is directed through second filter 28 into a corresponding first sensor 33 *a–h* in second sensor array 64 which in turn are electronically connected to microprocessor 80. As objects 100 are classified by microprocessor 80, air array 110 (or some other ejection mechanism) powered by compressor 112 ejects the bottles to be ejected into second bin 116 over divider 118 otherwise objects 100 which are not to be ejected fall into first bin 114. Objects 100 can be fed by conveyor 108.

As soon as one develops a system which uses a dual separation system, certain critical factors must be analyzed such as slides, angle, bottle speed, splitter position, and other mechanical features that depend upon the orientation of the machine.

Thus, although there have been described particular embodiments of the present invention of a new and useful System and Method for Distinguishing an Item from a Group of Items, it is not intended that such references be construed as limitations upon the scope of this invention except as set forth in the following claims.

What is claimed is:

1. A method for distinguishing an item into a first type or a second type comprising the steps of:
    a. transmitting electromagnetic radiation through said item;
    b. receiving said electromagnetic radiation passing through said item;
    c. splitting said received electromagnetic radiation into a first stream and a second stream;
    d. measuring said first stream at a first wavelength;
    e. measuring said second stream at a second wavelength,
    f. said first type comprises PET;
    g. said second type comprises PVC; and
    h. wherein said electromagnetic radiation comprises infrared radiation.

2. The method of claim 1 wherein:
    a. said first wavelength is substantially 1670 nanometers; and
    b. said second wavelength is substantially 1720 nanometers.

3. A method for distinguishing an item into a first type or a second type comprising the steps of:
    a. transmitting electromagnetic radiation through said item;
    b. receiving said electromagnetic radiation passing through said item;
    c. splitting said received electromagnetic radiation into a first stream and a second stream;
    d. measuring said first stream at a first wavelength;
    e. measuring said second stream at a second wavelength;
    f. said first type comprises clear containers; and
    g. said second type comprises light blue containers.

4. The method of claim 3 wherein said electromagnetic radiation comprises visible light.

5. The method of claim 3 wherein:
    a. said first wavelength is substantially 510 nanometers; and
    b. said second wavelength is substantially 633 nanometers.

6. A method for distinguishing an item into a first type or a second type comprising the steps of:
    a. transmitting electromagnetic radiation through said item;
    b. receiving said electromagnetic radiation passing through said item;
    c. splitting said received electromagnetic radiation into a first stream and a second stream;
    d. measuring said first stream at a first wavelengh;
    e. measuring said second stream at a second wavelength;
    f. said first type comprises PEN; and
    g. said second type comprises PET.

7. The method of claim 6 wherein said electromagnetic radiation comprises ultra-violet light.

8. The method of claim 6 wherein:
    a. said first wavelength is substantially 380 nanometers; and
    b. said second wavelength is substantially 400 nanometers.

9. A method for distinguishing an item into a first type or a second type comprising the steps of:
    a. transmitting electromagnetic radiation through said item;
    b. receiving said electromagnetic radiation passing through said item;
    c. splitting said received electromagnetic radiation into a first stream and a second stream;
    d. measuring said first stream at a first wavelengh;
    e. measuring said second stream at a second wavelength;
    f. splitting said received electromagnetic radiation into a third stream and a fourth stream;
    g. measuring said third stream at a third wavelength; and
    h. measuring said fourth stream at a fourth wavelength.

10. The method of claim 9 wherein:
    a. said first wavelength is substantially 380 nanometers;
    b. said second wavelength is substantially 390 nanometers;
    c. said third wavelength is substantially 430 nanometers; and
    d. said fourth wavelength is substantially 900 nanometers.

11. The method of claim 6 further sorting said items into a third type and a fourth type.

12. The method of claim 9 wherein:
    a. said first wavelength is substantially in the range of a blue-violet light color wavelength;
    b. said second wavelength is substantially in the range of a green color wavelength;
    c. said third wavelength is substantially in the range of a first red color; and
    d. said fourth wavelength is substantially in the range of a second red color.

13. A method for distinguishing an item into a first type or a second type comprising the steps of:
    a. illuminating said item with electromagnetic radiation;
    b. receiving the fluorescence emitted by said item;
    c. splitting said received fluorescence into a first stream and a second stream;
    d. measuring said first stream at a first wavelength;
    e. measuring said second stream at a second wavelength;
    f. wherein said electromagnetic radiation is black light;
    g. said first wavelength is substantially 390 nanometers; and
    h. said second wavelength is substantially 425 nanometers.

* * * * *